United States Patent [19]

Cohen et al.

[11] Patent Number: 4,591,496

[45] Date of Patent: May 27, 1986

[54] PROCESS FOR MAKING SYSTEMS FOR THE CONTROLLED RELEASE OF MACROMOLECULES

[75] Inventors: Jonathan M. Cohen, Elmont, N.Y.; Ronald Siegel, Arlington Hts.; Robert Langer, Somerville, both of Mass.

[73] Assignee: Massachusetts Institute of Technology, Cambridge, Mass.

[21] Appl. No.: 571,007

[22] Filed: Jan. 16, 1984

[51] Int. Cl.⁴ .................... A61K 31/74; A61K 9/28; A61K 9/22; A61K 9/26

[52] U.S. Cl. ..................... 424/15; 264/109; 264/123; 264/125; 424/14; 424/16; 424/19; 424/22; 424/78

[58] Field of Search ............ 424/14, 16, 19, 22, 424/78, 15; 264/109, 123, 125

[56] References Cited

U.S. PATENT DOCUMENTS

| | | | |
|---|---|---|---|
| 2,757,124 | 7/1956 | Wolff | 424/16 |
| 3,096,248 | 7/1963 | Rudski | 424/16 |
| 3,308,217 | 3/1967 | Lowy et al. | 264/117 |
| 3,670,065 | 6/1972 | Eriksson et al. | 264/131 |
| 4,151,273 | 4/1979 | Riegelmon et al. | 424/78 |
| 4,164,560 | 8/1979 | Folkman et al. | 424/22 |
| 4,179,497 | 12/1979 | Cohen et al. | 424/22 |
| 4,357,312 | 11/1982 | Hsieh et al. | 424/15 |

OTHER PUBLICATIONS

Little et al., "Tablet Making," 2nd ed. (1963), Northern Pub. Co., Liverpool, England, pp. 11–23, 29–33.

*Primary Examiner*—Shep K. Rose
*Attorney, Agent, or Firm*—Arthur A. Smith, Jr.; Paul J. Cook

[57] ABSTRACT

A new method for making polymeric systems for the sustained release of macromolecular drugs is described. The method consists of mixing drug and polymer, e.g. ethylene-vinyl acetate copolymer powders below the glass transition temperature of the polymer, and compressing the mixture at a temperature above the glass transition point. The macromolecule is not exposed to organic solvent during the fabrication process. The sustained release and bioactivity of macromolecules is unchanged throughout the pressure casting and release processes.

7 Claims, 2 Drawing Figures

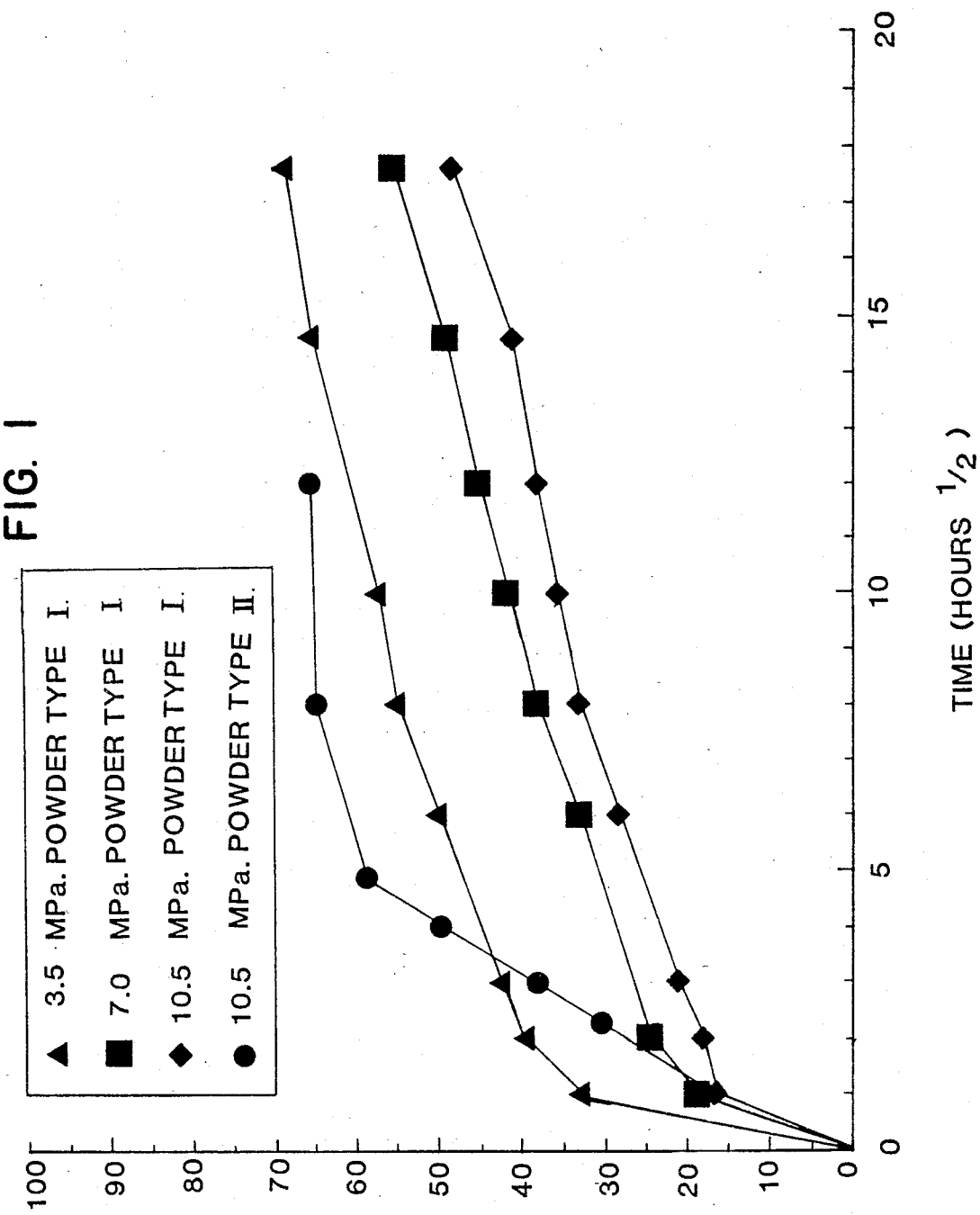

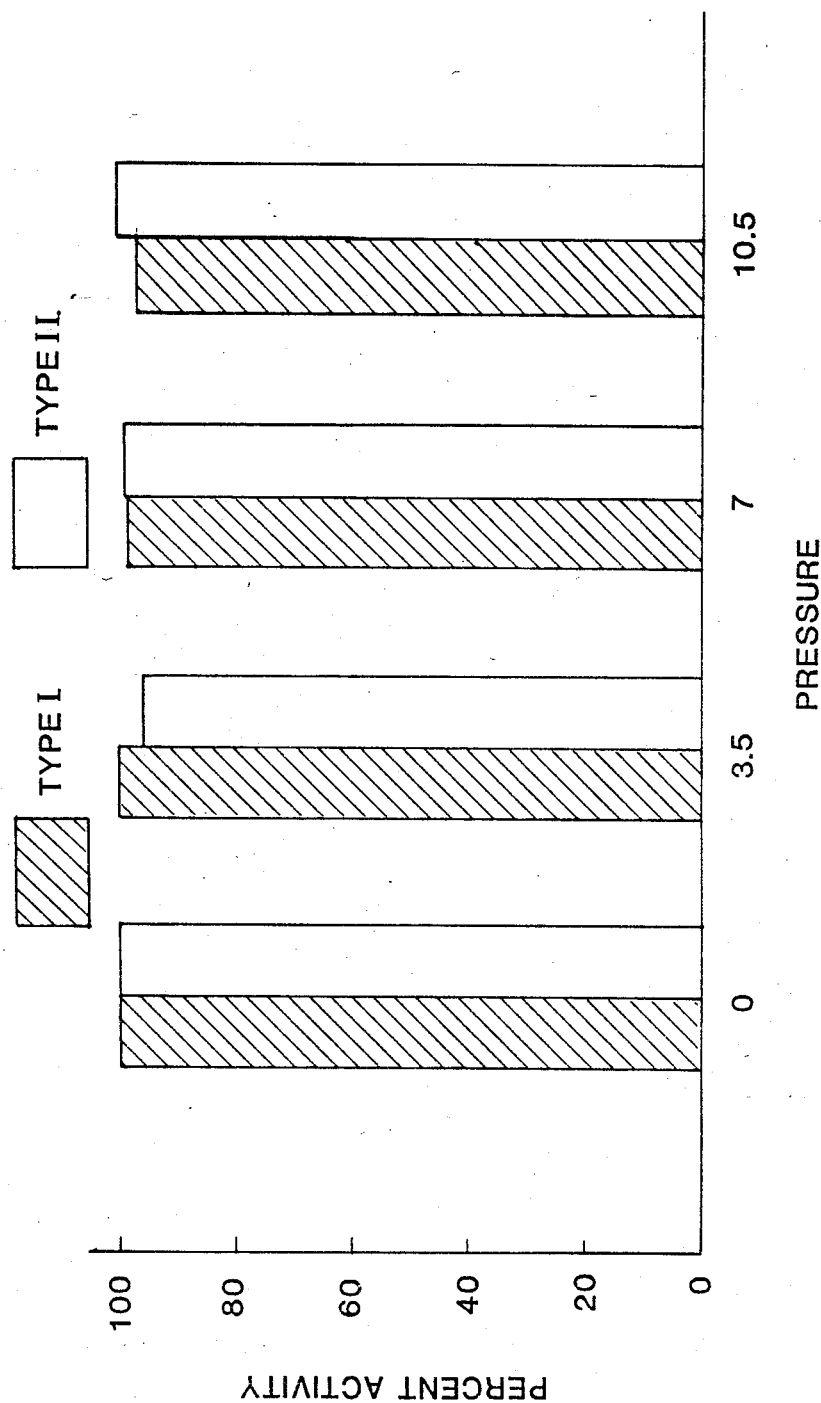

PROCESS FOR MAKING SYSTEMS FOR THE CONTROLLED RELEASE OF MACROMOLECULES

The invention described herein was made with partial support provided from a grant or award from the National Institute of Health, GM 26698.

FIELD OF THE INVENTION

This invention relates to both novel and useful systems for delivering macromolecules. More particularly, the invention pertains to systems in the form of polymeric compositions useful for the controlled and continuous delivery of water swellable, biologically active macromolecules from a polymer matrix having limited water sorptivity over prolonged periods of time.

BACKGROUND OF THE INVENTION

In recent years, much research has been done in developing systems using polymeric compositions for the programmed release of active agents, especially drugs, over periods of time. The purpose of these systems is to dispense the agent at a controlled, and if desired, constant rate in order, as in the case of pharmeutical agents or drugs, to improve therapy by presenting the drug in the most beneficial and reliable manner, with a minimum possibility of complications from the drug or from failure to comply with the therapeutic regimen. For example, see Folkman, et al, in Journal of Surgical Research, Vol. 4, pages 139 to 142, 1964; U.S. Pat. No. 3,832,252 issued to Higuchi, et al; and U.S. Pat. No. 3,854,480 issued to Zaffaroni. Both of these patents are assigned to the Alza Corporation of Palo Alto, Calif.

While the above systems represent an extraordinary advancement in the art, and while they possess ideal kinetics for effectively delivering low molecular weight agents, a limiting feature associated with these systems is they are not designed to deliver agents which possess macromolecular structures. This is so since such systems operate, in the case where the polymer matrix is not absorbable in the environment, by diffusion which fundamentally depends on the agent permeating at a controlled rate through the polymer. Inasmuch as macromolecular agents do not diffuse through polymeric materials at rates which are high enough to be used to advantage, these prior art systems cannot be used satisfactorily for delivering macromolecular agents. It is also disclosed in U.S. Pat. Nos. 3,896,819 and 3,948,254, issued to Zaffaroni and assigned to the Alza Corporation, that certain large molecules can be released by the delivery devices as defined therein; however, the devices of these patents are structurally distinct, operate differently, and accordingly they do not provide the beneficial release kinetics as obtained with the system of this invention.

It is apparent from the foregoing presentation that a critical need exists for systems that can successfully deliver macromolecular agents. The prior art has made systems that seemingly attempted to satisfy this need, but the results obtained have not led to acceptable application of the systems. For example, Davis in the "Control of Diabetes with Polyacrylamide Implants Containing Insulin", Experientia, Vol. 28, page 348, 1972 and in "Diffusion in Polymer Gel Implants", Proc. Nat. Acad. Sci., USA, Vol. 71, pages 3120 to 3123, 1974 disclosed gels formed of crosslinked, hydrophilic polyacrylamide and polyvinylpyrrolidone polymers containing protein solutes used as implants that release the solutes by simple diffusion over a limited period of time. However, these single phase gel compositions did not lead to systems having accaptable release properties because the duration of release depends on the density of the gel which property is difficult to control with standard manufacturing techniques, and also because the rate of solute release follows an exponential time course until depletion of the solute is virtually complete. Similar attempts to release macromolecules were disclosed by Gimbrone, et al in "Tumor Growth and Neovascularization: An Experimental Model Using the Rabbit Cornea", in J. Nat. Can. Inst., Vol. 52, pages 413 to 427, 1974, with the use of polyacrylamide gels for delivering tumor angiogenesis factor, and by Gould et al, in U.S. Pat. No. 3,576,760. In the patent, Gould et al disclosed the entrapment of enzymes in water soluble acrylic polymers which compositions release the enzyme upon contact with water by virtue of dissolution of the water soluble polymer. None of the prior art references has lead to an acceptable system for releasing macromolecular structures, particularly biologically active molecules of increased size and weight at controlled rates over prolonged periods of time.

Folkman et al, U.S. Pat. No. 4,164,560, hereby incorporated by reference, describes a method of making such a body by forming a liquid mixture containing the polymer, the active substance, and an organic solvent capable of dissolving the polymer, and solidifying the liquid mixture to form the polymeric body. Folkman et al have shown that controlled release systems for macromolecules can be formulated by dissolution of ethylene-vinyl acetate copolymer in an organic solvent (dichloromethane), adding powdered macromolecule, casting the mixture in a mold at low temperature, and vacuum drying. However, the addition of solvent during the casting procedure may cause denaturation of certain macromolecules. In addition, the removal of the casting solvent in the drying step is time consuming and leads to shrinkage and possibly shape distortion of the matrix. Therefore, it would be highly desirable to provide a process for making these release systems without the need for a solvent.

SUMMARY OF THE INVENTION

In general, the invention features an improved method of making such a body, in which a biologically active material and the polymer below the glass transition temperature of the polymer and compressing the mixture above the glass transition point of the polymer.

In preferred embodiments, the polymer is an ethylene-vinyl ester copolymer of the general formula:

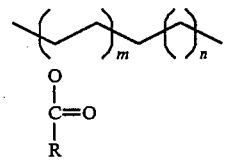

wherein R is hydrogen, lower alkyl of 1 to 7 carbons, or aryl, m is 10 to 40% by weight, and n is (100 m) % by weight; and the biologically active substance is an enzyme, a hormone, an enzyme inhibitor, an antigen, or a drug.

The new method provides substantial advantages including elimination of shrinkage of the mixture during formation, eliminates the need for exposing the biologically active material to a solvent, elimination of solvent removal and reduction of processing time.

Additional advantages and features of the invention will be apparent from the following description of the preferred embodiments thereof, and from the claims.

DETAILED DESCRIPTION OF THE INVENTION

It should be understood that the detailed description and specific examples, while indicating preferred embodiments of the invention, are given by way of illustration only, since various changes and modifications within the spirit and scope of the invention will become apparent to those skilled in the art from this description and the accompanying claims.

The term "matrix" as used herein denotes a carrier polymeric phase of the interpenetrating phase with the matrix comprising a polymer that is biocompatible and sufficiently resistant to chemical and/or physical attack by the environment of use, such that the matrix remains substantially intact throughout the prolonged period of time the macromolecule is released from the system.

The polymer matrices, which are suitably used in the present invention, are biocompatible in the environment of use, plastically deformable, have limited water sorptivity, and they are substantially impermeable to the passage of biologically active macromolecular materials in admixture therewith. Additionally, while the amount of water sorption needed to obtain optimum release varies with the specific polymer matrix, generally the useful and preferred polymers suitable for forming the matrix will absorb a maximum of not greater than about 50% by weight of water to form the system and obtain the desired macromolecular release properties. Preferably, the sorptivity of the polymer matrix is between 30% and 50% by weight of water and in a still more preferred embodiment the sorptivity of the polymer matrix is less than 30% by weight of water. The term "water" as used herein includes biological fluids, saline and physiologically acceptable buffer.

Typical polymeric material suitable for forming the matrix and having the above-described water sorption, expressed as a weight percentage of the initial dry weight at the temperature of use, are the naturally occurring and synthetic commercially available polymers. They include acyl substituted cellulose acetates and alkyl derivatives thereof; partially and completely hydrolyzed alkylene-vinyl acetate copolymers; unplasticized polyvinyl chloride; crosslinked homo- and copolymers of polyvinyl acetate; crosslinked polyesters of acrylic and methacrylate; polyvinyl alkyl ethers; polyvinyl fluoride; silicone; polycarbonate; polyurethane; polyamide; polysulphones; styrene acrylonitrile copolymers; crosslinked poly(ethylene oxide); poly(alkylenes); poly(vinyl imidazole); poly(esters); poly(ethylene terephthalate); and chlorosulphonated polyolefins.

In a presently preferred embodiment, the polymeric materials useful for forming the matrix are the ethylenevinyl ester copolymers of the general formula:

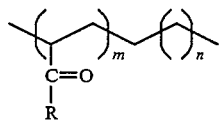

wherein R is hydrogen, lower alkyl of 1 to 7 carbons and aryl and m is (10 to 40) % by weight and n is (100 m) % by weight. Typical alkyl groups include ethyl, propyl, isopropyl, tert-butyl, pentyl and hexyl. Typical aryl groups include phenyl. Representative ethylene-vinyl ester copolymers suitable for forming the matrix, with the copolymers named as the acetates, include ethylene-vinyl acetate, ethylene-vinyl methylacetate, ethylene-vinyl ethylacetate, ethylene-vinyl propylacetate and the like. In its broadest aspects, the present invention contemplates the use of ethylene-vinyl ester copolymers having a melt index of about 0.5 to 100 grams per ten minutes, a density of 0.920 to 1.00, and a frequency of acyl, for example acetoxy groups, on the polyethylene backbone of 1/70 to ⅛. In a preferred embodiment, the copolymer is ethylenevinyl acetate having a vinyl acetate content of about 10 to 50% by weight, a melt index of about 0.5 to 259 grams per ten minutes, a density having a range of about 0.920 to 0.980, and a frequency of acetoxy groups on the polyethylene backbone of 1/70 to ⅛. Typical water sorptivities for ethylene-vinyl acetate copolymers having a vinyl content of 10%, 30% and 40% are 0.015%, 0.25% and 0.67% respectively. The ethylene-vinyl ester copolymers are known, commercially available materials and exemplary techniques for their preparations are described in U.S. Pat. Nos. 2,200,429, 2,396,785 and 2,947,735, in British Pat. Nos. 569,927 and 582,093, and in Crystalline Olefin Polymers, Edited by Raff, R. A. V., and Doak V. W., Part II, pages 261 to 266, 1964, published by Interscience Publishers, Inc., New York.

The biologically active macromolecules that can be suitably employed in accordance with the invention with warm blooded animals including humans, veterinary animals, and farm animals are macromolecules that are swellable in water and biological fluids and have a molecular weight of at least 1000. Exemplary macromolecules include proteins such as the peptide hormones that circulate in the blood of warm blooded animals such as insulin, glucagon, parathyroid and pituitary hormones, calcitonin, vasopressin, renin, prolactin, growth hormone, thyroid stimulating hormone, corticotrophin, follicle stimulating hormone, luteinising hormone and chorionic gonadotrophin. Other macromolecules include the physiologically active enzymes transferases, hydrolases, lysases, isomerases, protease, ligases and oxidoreductases such as seterases, phosphatases, glycosidases and peptidases and the enzyme inhibitors such as leupeptin, antipain, chymostatin and pepstatin. Other macromolecules within the molecular weight range of $10^3$ to $10^6$ daltons suitable for release according to the invention include, wherein M.W. is molecular weight, soybean trypsin inhibitor (M.W. 21,000), for example aprotinin, lysozyme (M.W. 14,000), catalase (M.W. 250,000) alkaline phosphatases (M.W. 88,000), tumor angiogenesis factor, cartilage factor (M.W. 16,000) and similar proteins and drugs.

The relative proportions of the biologically active macromolecule incorporated into the matrix to form the two-phase system, can be varied over a wide range depending on the macromolecule to be administered and the desired effect. Generally, the macromolecule can be present in an amount which will be released over controlled periods of time according to predetermined desired rates. This necessarily implies a quantity of macromolecule greater than the standard single dosage. Proportions suitable for the purpose of the invention can range from 3 to 90 parts by weight of macromolecule to 97 to 10 parts by weight of polymeric matrix. A preferred ratio includes 15 parts by weight of macromolecule formulated with sufficient polymeric matrix to give 100 parts by weight of system. A more preferred embodiment comprises 25 to 80 parts by weight of macromolecule mixed with up to 100 parts by weight of a polymeric matrix which forms the two-phase system of the invention.

The expression, "limited water sorptivity of the polymer matrix", as used herein is important as it denotes the ability of a selected polymer to function for the system of this invention. One procedure for determining water absorption of a given polymer comprises immersing a dry, measured section of polymer in water at 20° C. for 24 hours, and after its removal from water reweighing the polymer and expressing the gain in weight, as percent by weight of polymer, of water absorbed. Detailed procedures for measuring the water sorptivity of polymers are described in the Handbook of Common Polymers, Edited by Scott, J. R. and Roff, W. J., Section 61 1971, published by Chemical Rubber Press, Cleveland, Ohio; by Daynes, H. A., in Trans. Faraday Soc., Vol. 33, pages 531 to 544, 1933; in Polymer Handbook, Edited by Brandrup, J., and Immergut, E. H., Sections VI-33 and 88, 1967, published by Interscience Publishers, Inc., New York; and according to ASTM Section D-570.

The term "swellable" as used herein denotes a functionality of a macromolecule to expand or increase in physical size in the presence of swelling agents, mainly aqueous type fluids such as water and biological fluids. One procedure for measuring the swellability or the rate of swelling of a macromolecule comprises placing a known sample in the environment of a swelling agent at a known temperature and for a given time; then, after removing the sample from the environment, measuring its change in dimensions followed by drying it and measuring it in the dry state. A method for determining swelling is disclosed in Coll. Czech. Chem. Commun., Vol. 24, pages 349 to 353, 1969, and the references cited therein; and in Polymer Chemistry, by Vollmert, B., pages 547 to 548, 1973, published by Springer-Verlag, New York.

The expression melt index as used herein denotes the number of grams of copolymer which can be forced through a standard cylindrical orifice under a standard pressure at a standard temperature and thus it is inversely related to the molecular weight. As used in this specification and the appended claims, melt index is as determined in accordance with standard ASTM D-1238-65T condition E practice.

In accordance with the present invention, macromolecules are released at a controlled and continuous rate over a prolonged period of time. While not being bound by any particular theory, what makes the mechanism of release of macromolecules from the polymer matrix noteworthy and unexpected is that it cannot be explained by traditional concepts of diffusion. When the systems of this invention are placed in an aqueous environment, water will permeate by diffusion into the polymer matrix and be absorbed by the biologically active macromolecules. Since the macromolecules in question are ultimately molecularly dispersible in water, the dispersed particles will tend to swell as they absorb water. Since, however, the polymer matrix with which they are surrounded has little water-sorptivity, the swelling process is retarded by tensile stresses in the matrix. Nonetheless, the swelling pressure induced by the macromolecules causes gradual creep and relaxation of the matrix, allowing the particles to slowly sorb increasing amounts of water and increase in volume. Ultimately, a gelatinous, highly concentrated macromolecule solution will create channels or micropores in the matrix directly communicating with the external environment.

Then, residual stress in the plastically deformable matrix will tend to express gel-like macromolecule concentrate with bulk-flow delivery. Once this process has ceased, there can be further slow imbibtion and swelling of the residual macromolecular gel, with further expulsion of macromolecules, and ultimately, when the residual macromolecular gel remaining in the pore spaces becomes sufficiently diluted to permit free diffusion of macromolecules, the macromolecules will be released by molecular diffusion through water within the pore spaces of the matrix. Since diffusion coefficients for macromolecules in water are very low, of the order of $10^{-7}$ to $10^{-9}$ cm$^2$/sec, such systems may be expected to release at very low rates over very long time periods, as is observed. While zero-order release behavior is limited for these kinds of systems, they are nonetheless very useful for delivery of very potent substances at very low rates over very long time periods.

The systems of this invention can be manufactured in the form of delivery systems shaped as devices that can take a wide variety of shapes, sizes and forms for delivering numerous active and beneficial macromolecules to different environments of use. For example, the systems can be made as devices including buccal and oral devices; vaginal and intrauterine devices of cylindrical, bullet, elliptical, circular, bulbous, loop, bow or any other shape that lends itself to placement in these biological environments; the devices also include ocular devices of any geometric shape for comfortable placement in the cul-de-sac such as ellipsoid, bean, banana, circular, rectangular, doughnut, crescent, and half ring shaped devices. In cross-section, the ocular devices can be doubly convex, concavo-convex and the like. The dimensions of the ocular devices can vary according to the size of eye, with satisfactory eye devices generally having a length of 4 to 20 millimeters, a width of 1 to 15 millimeters and a thickness of 0.1 to 4 millimeters. Other devices made according to the spirit of the invention include implants, anal, pessaries and prosthestic devices, artificial glands for dispensing a pharmaceutically acceptable macromolecular agent having a physiological function essentially equivalent to a corresponding natural gland, cervical, nasal, ear and skin devices.

The formulations of this invention are formed by first mixing the biologically active molecule and the polymer at a temperature below the glass transition temperature of the polymer and below the temperature at which substantial degradation of the biologically active molecule occurs. Thereafter, polymer and biologically active molecule are formed at a temperature above the glass transition temperature of the polymer and below the temperature at which substantial degradation of the biologically active molecule occurs. The choice of a particular polymer for a given biologically active molecule can be easily made by the person skilled in the art given this temperature criteria.

EXAMPLE I

Polymer Glass Transition Temperature

The glass transition temperature of Ethylene-Vinyl Acetate Copolymer was determined experimentally using a Differential Scanning Calorimeter.

Matrix Preparation

Ethylene-vinyl acetate copolymer was converted into a powder by one of two methods. The first method involved the dissolution of 3 grams ethylene-vinyl acetate copolymer in 20 ml of dichloromethane. The solution was extruded dropwise into a 250 ml beaker containing 100 ml of liquid nitrogen using a 5 cc syringe that was fitted with a hypodermic needle. From this time on, all instruments that came into contact with the frozen polymer solution were cooled with liquid nitrogen, and wherever possible, precooled in a freezer to minimize the quantity of liquid nitrogen necessary for cooling.

The frozen droplets were ground for 5 minutes with a mortar and pestle. The powder was then spread evenly over three 8"×8" glass sheets that had been cooled to −10° C. The glass sheets were returned to a −10° C. freezer for two hours. At the end of that time, most of the solvent had evaporated, leaving a stringy powder. This powder was removed with a razor blade, bathed in a 100 ml pyrex beaker with 30 ml of liquid nitrogen, and then ground to a fine powder with a mortar and pestle as before. This powder was placed under vacuum for two hours. No effort was made to separate powder granules on the basis of particle size. Polymer powder prepared by this method will be referred to as "Powder Type I".

In the second method of powder preparation, 20 grams of ethylene-vinyl acetate copolymer beads were cooled in 40 ml liquid nitrogen and placed in an electric mill. The mill was set for 90 second grinding intervals. Between grindings, the polymer beads were cooled with 20 ml portions of liquid nitrogen. During the grinding process cold nitrogen vapor was circulated around the sample chamber through the chamber's cooling ducts. The powder collects around the outer edges of the sample chamber, and can be extracted with a spatula after the second grinding, and after every successive grinding. After the eighth grinding, approximately 4 grams of frozen pellets were added to restore the original volume. This process was repeated until sufficient powder was collected to prepare the samples. The ground polymer powder was then sieved to specific size ranges using a stack of graduated sieves, in an automatic sieve shaker at −40° C. Polymer powder prepared by this second method will be denoted "Powder Type II".

To formulate the controlled release system, macromolecular drug powder was sieved to a 90–180 μm particle size range. Then, macromolecule and polymer powders were placed in a plastic weighing boat which was then transferred to a pyrex baking dish containing liquid nitrogen at a depth of 1 cm. The powders were mixed in the weighing boat for 5 minutes with a spatula that was chilled with liquid nitrogen. After mixing, the powders were poured into a piston mold. The mold was chilled in a −10° C. freezer for one hour, and then chilled with 20 ml liquid nitrogen immediately before the powder mixture was poured in. After the mixed powder was poured into the piston, the piston mold assembly was warmed to 37 degrees in an oven for 1 hour and then placed in a hydraulic press. The pressure on the mold was increased during a 90 second interval from zero pascals to the maximum pressure desired. After 30 minutes, the pressure was released, leaving a cohesive, heterogeneous glass-like slab.

The slab was removed from the mold with the aid of a scalpel and forceps. Any of the mixture that may have been extruded during the pressurization was trimmed with the scalpel. The slab was then gently peeled from the mold with the forceps.

Slabs were prepared separately at maximum pressures of 3.5 MPa (Megapascals), 7 MPa, and 10.5 MPa. Macromolecules tested for release were bovine serum albumin (BSA) and trypsin.

Kinetics

Small (0.5 cm$^2$) pieces of the glass-like slab were cut with a scalpel and tested for release as follows: Scintillation vials were filled with 10 ml of physiological saline for BSA release studies and 10 ml of TRIS buffer for trypsin release studies. The glass-like matrix samples were attached to glass loops made from pasteur pipettes that were fitted into scintillation vial caps. The samples were attached by passing a thread of 4/0 silk through the sample orthogonal to the face of the slab. Tying the sample to the rod insures that the sample was always bathed on all sides with fluid, and provides an easy way to transfer the samples from vial to vial during the release study. Release kinetics for BSA were determined by UV spectrophotometry as described on sixteen 25% wt/wt loaded BSA slabs.

Bioactivity

Trypsin release (8 slabs) was assayed by UV spectrophotometry for protein content after 25–36 hours of release. The released trypsin was then diluted with TRIS buffer to a concentration of 0.11 mg/ml. The enzyme turnover rate of the diluted trypsin solution on a Tosyl-Arginine-Methyl-Ester (TAME) substrate was then tested at 247 nm. The turnover rate of the test solution was compared to the turnover rate of a standard trypsin solution at the same concentration. The bioactivity index was taken to be the ratio of the two turnover rates.

A test was also done to check bioactivity as a function of release duration. Bioactivity was assessed at 9 different times over a period of 310 hours for 5 different matrices cast with Powder Type I at a pressure of 10.5 MPa.

RESULTS

Kinetics

The release kinetics for matrices of 25 percent (wt/wt) BSA are shown in FIG. 1. Release kinetics in FIG. 1 for 25% (wt/wt) BSA slabs are:

(▲) Powder Type I, Formation Pressure 3.5 MPa.
(■) Powder Type I, Formation Pressure 7.0 MPa.
(♦) Powder Type I, Formation Pressure 10.5 MPa.
(●) Powder Type II, Formation Pressure 10.5 MPa.

There is a burst effect at the beginning of the release for Powder Type I. The magnitude of the burst decreases with higher formation pressure, although the final release rate seems unaffected. No burst effect is seen for matrices formulated with Powder Type II. However, the release rate is much higher in this case than it is for matrices cast with Powder Type I.

Bioactivity

FIG. 2 shows the bioactivity index of released trypsin after 25-36, as a function of formation pressure and of polymer powder type. The bioactivity index in all cases exceeds 97%. There appears to be no difference between polymer powder types in their effect on enzyme activity. When the bioactivity index of released trypsin was measured as a function of release time, it exceeded 95% in every case.

Polymer Glass Transition Temperature

The glass transition temperature was $-36.5°$ C.

The advantages of pressure casting, when compared to solvent casting, include:

(1) Elimination of shrinkage, (2) Lack of the necessity to expose the macromolecule to solvent, (3) Elimination of the need for potentially expensive scale up steps such as vacuum drying, and (4) Reduction of processing time. (Slabs have been produced in 2 hours compared to 4 days required for solvent casting.)

In addition, polymer Powder Type II provides the opportunity to cast matrices without using any organic solvent at all.

Increasing formation pressure decreases the initial burst of release when Powder Type I is used. This is probably due to the requirement of high pressure to insure fusion of polymer granules. At low formation pressure the polymer matrix is grainy. The boundaries between polymer grains may provide extra channels through which drug can diffuse. The difference in the release kinetics for polymers cast with different powder types may be due to the fact that Powder Type II was sieved to a relatively narrow particle size range, while Powder Type I was not. Thus, use of Powder Type II may lead to a more regular channel structure and, hence, more regular release kinetics.

We claim:

1. A method for making a glass-like matrix useful as a delivery system for the controlled release of biologically active substances comprising the steps of:

preparing a polymeric material in powder form at a temperature below its glass transition temperature, said polymeric material having limited water sorptivity;

preparing a swellable biologically active substance in powder form at a temperature less than the minimal temperature at which substantial degradation of the substance occurs;

combining said polymeric material powder and said biologically active substance powder as a mixture in ratios ranging from 97-10 parts polymeric material powder by weight to 3-90 parts biologically active substance powder by weight; and compressing said mixture to form a solid, glass-like matrix, said compression occurring at a temperature greater than the glass transition temperature of said polymeric material but less than the minimal temperature for substantial degradation of said biologically active substance.

2. In the method of claim 1, the improvement wherein said polymer is an ethylene-vinyl ester copolymer of the general formula

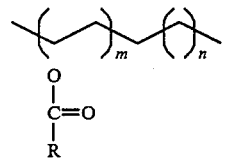

wherein R is hydrogen, lower alkyl of 1 to 7 carbons, or aryl, m is (10 to 40) % by weight and n is (100-m) % by weight.

3. In the method of claim 1, the improvement wherein said biologically active substance is an enzyme.

4. In the method of claim 1, the improvement wherein said biologically active substance is a hormone.

5. In the method of claim 1, the improvement wherein said biologically active substance is an enzyme inhibitor.

6. In the method of claim 1, the improvement wherein said biologically active substance is an antigen.

7. In the method of claim 1, the improvement wherein said biologically active substance is a drug.

* * * * *